United States Patent [19]

Kopchick et al.

[11] Patent Number: 4,828,987

[45] Date of Patent: * May 9, 1989

[54] AVIAN RETROVIRUS-BOVINE GROWTH HORMONE DNA

[75] Inventors: John J. Kopchick, Verona; Frederick C. Leung, Scotch Plains; Thomas J. Livelli, Lyndhurst; Richard H. Malavarca, South Orange, all of N.J.

[73] Assignee: Merck & Co., Inc., Rahway, N.J.

[*] Notice: The portion of the term of this patent subsequent to Aug. 11, 2004 has been disclaimed.

[21] Appl. No.: 609,923

[22] Filed: May 14, 1984

[51] Int. Cl.$^4$ .................. C12P 21/00; C12P 19/34; C12N 15/00; C12N 7/00
[52] U.S. Cl. .................................. 435/68; 435/91; 435/172.3; 435/317.1; 435/320; 435/235; 435/240.1; 536/27; 935/13; 935/32; 935/34; 935/57; 935/60
[58] Field of Search ............... 435/172.3, 68, 91, 317, 435/70, 235, 236, 320, 317.1, 240.1, 240.2; 935/13, 22, 33, 34; 536/27

[56] References Cited

U.S. PATENT DOCUMENTS 4,405,712  9/1983  Vande Woude .................. 435/5
4,686,098  8/1982  Kopchick et al. ................ 424/424

FOREIGN PATENT DOCUMENTS

84/01150  3/1984  World Int. Prop. O. ........... 435/68

OTHER PUBLICATIONS

German et al. (1982) *Proceedings National Academy Sciences, U.S.A.* vol. 79, pp. 6777–6781.
Kopchick, J. et al. 1985, DNA 4:23.
Gorman, C. et al. Nov. 1982, PNAS 79:6777.
Joyner, A. et al. Mar. 1982, PNAS 79:1573.
Sompayrac, L. and K. Danna, 1981, PNAS 78:7575.
American Type Culture Collection, Catalog of Strains II 1983, 4th Edition, p. 62.
Goeddel, D. et al. Oct. 1979, Nature 281:544.
Doehmer, J. et al. 1982, PNAS 79:2268.
Woychik, R. et al. 1982, NAR 10:7197.
Gubler, U. et al., Jul. 1983, PNAS 80:4311.
Palmiter et al., Nature 300:611–615 Dec. 16, 1982.
Bates et al., Endocrinology 71:345–360 Sep. 1962.

*Primary Examiner*—Thomas G. Wiseman
*Assistant Examiner*—Stephanie Sedman
*Attorney, Agent, or Firm*—Frank S. Chow; Donald J. Perrella; Hesna J. Pfeiffer

[57] ABSTRACT

Recombinant DNA molecules in which an avian retroviral long terminal repeat (LTR) has been ligated to the bovine growth hormone gene are described herein. The retroviral LTR was derived from a plasmid clone of a Schmidt Rupin strain of Rous Sarcoma Virus while the bovine growth hormone (BGH) gene was derived from a lambda-bacteriophage genomic library. Using a transient eucaryotic expression assay system, the plasmid constructs were screened for their ability to direct expression and secretion of bovine growth hormone. These constructs were co-transformed into a mammalian cell (mouse) culture in order to obtain a stable cell culture secreting large amounts of bovine growth hormone.

5 Claims, 2 Drawing Sheets

AVIAN RETROVIRUS-BOVINE GROWTH HORMONE DNA

BACKGROUND OF THE INVENTION

The present invention is directed to the preparation and use of novel recombinant DNA molecules in which an avian long terminal repeat (LTR) is ligated to the bovine growth hormone (BGH) gene. Stable mouse fibroblast cell lines have been generated which contain the recombinant genetic material integrated into the mouse cell genome, and which are valuable for production of large amounts of biologically active BGH.

U.S. Pat. No. 4,405,712 describes the use of the LTR vector for activating the expression of a desired gene. Activation is achieved by (1) isolating tee desired gene; (2) ligating to the gene a vector comprising the LTR sequences from a retroviral provirus genome, thus providing a hybrid gene; (3) inserting the hybrid gene into a mammalian recipient cell using DNA transfection; and (4) screening the cells for the phenotype of the gene. The LTR vector can be linked to the gene of interest by conventional recombinant techniques and serves as a marker for identification and cloning of the gene by standard recombinant DNA cloning procedures.

The cloning and sequencing of the bovine growth hormone gene is described in the article Woychik et al., Nucleic Acids Research, Vol 10, Nov. 22, 1982, pp. 7197–7210, see also Keshet et. al., Nucleic Acids Research, Vol 9, Nov. 1, 1981, pp. 19–30. The nucleotide sequencing of a variety of avian retroviral LTRs is described by Bizub, Katz and Skalka, J. Virology, 49:557–565, Feb. 1984.

BRIEF DESCRIPTION OF THE DRAWINGS

FIG. 1-B is the restriction map of the recombinant plasmid, pBGH-2. This plasmid is pBGH-1 without the BGH 5' flanking region.

FIG. 1-C is the restriction map of the recombinant plasmid, pBGH-3, also found in FIG. 2.

FIG. 1-D is the restriction map of the recombinant plasmid, pBGH-4.

SUMMARY OF THE INVENTION

Figure 1:
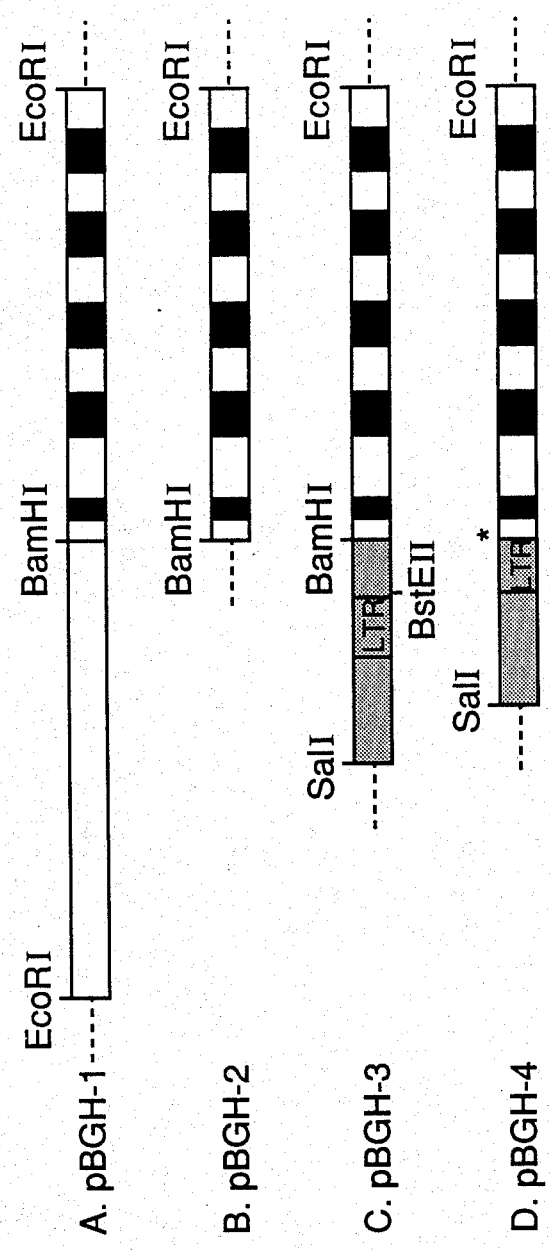
FIG. 1-A is the restriction map of the recombinant plasmid, pBGH-1. The plasmid (in pBR 322) contains the BGH structural gene sequence 5' flanking regions which usually contain the promoter and enhancer elements, as well as 3' flanking regions.
Figure 2:
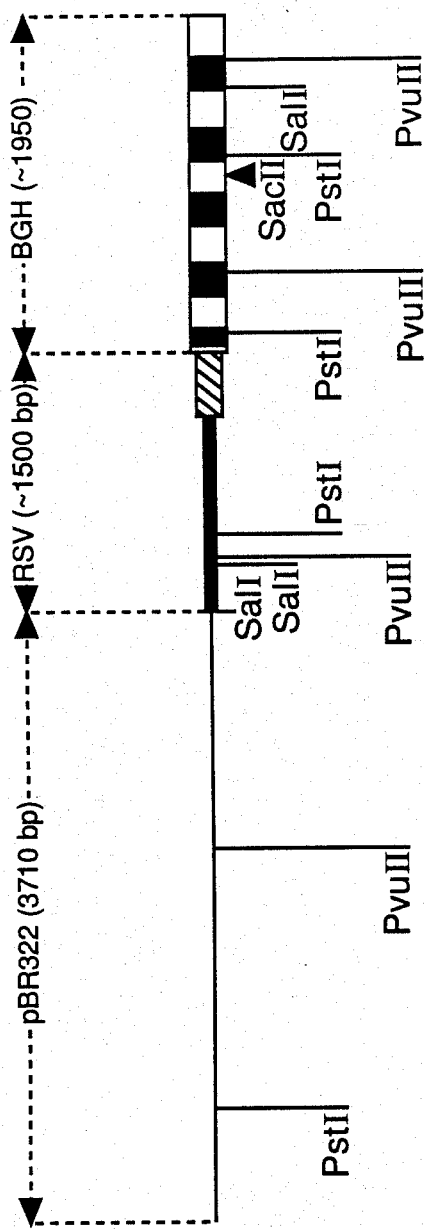

Using recombinant DNA techniques, portions of the bovine growth hormone structural gene have been combined with eucaryotic regulatory regions of the Rous Sarcoma Viral genome to produce the novel materials herein designated as pBGH-3 and pBGH-4.

DETAILED DESCRIPTION

Construction of Bovine Growth Hormone-Avian Retroviral DNA hybrids

We have obtained bovine growth hormone genomic DNA in a pBR322 plasmid (pBGH-1) Using recombinant DNA technology, the bovine growth hormone promoter element was removed from the structural gene. This subcloned plasmid lacking a promoter was termed pBGH-2 We have ligated an avian retroviral promoter element, i.e., a viral Long Terminal Repeat (LTR), to the bovine growth hormone structural gene. Ligation was performed at 2 distinct restriction enzyme cleavage sites found within a region of each DNA which encodes 5'-untranslated portions of their m-RNAs. These 5'-untranslated portions of the m-RNAs ("leader" sequences) are nucleotides located between the m-RNA cap site and the translation initiation codon. Bovine growth hormone and avian retroviral 5'-untranslated nucleotide sequences are comprised of 59 base pairs and 379 base pairs, respectively.

These novel plasmid clones have been named pBGH-3 and pBGH-4.

Construction of Recombinant Plasmid, pBGH-3

Plasmid DNAs (bovine growth hormone and Rous Sarcoma Virus) were transfected into E. coli RR1 cells. Clones were isolated and the plasmid DNAs amplified. The resulting DNAs were characterized using diagnostic endodeoxyribonuclease recognition sites based on restriction enzyme maps available for the original 0105 clones. We have termed these plasmids. pBGH-1 (plasmid bovine growth hormone-1) and pL397 (Rous Sarcoma Virus)

pBGH-1 (10 μg) was digested to completion with Bam HI and SalI. Two linear DNA fragments of 5.0 kb and 3.0 kb resulted. The fragments were separated by agarose gel electrophoresis (1% Seaplaque agarose). The larger fragment containing the bovine growth hormone gene was eluted from the gel. To insure purity, this DNA again was subjected to agarose gel electrophoresis (1% Seaplaque) and elution. Approximately 500 ng was recovered.

Rous Sarcoma virus clone pL397 was enzymatically cleaved with BamHI and the five resulting linear DNA fragments separated by agarose gel electrophoresis (1% Seaplaque). A linear fragment of 6.0 kb was eluted from the gel, enzymatically digested with SalI, and subjected to a similar agarose gel electrophoresis procedure. Approximately a 2.0 kb linear DNA fragment encoding the avian retroviral LTR (promoter) was purified Approximately, 500 ng of DNA was recovered.

Ligation of the viral DNA sequences to the bovine growth hormone gene occurred at the unique BamHI site. Viral sequences include the 3' portion of the 'env' gene, the viral LTR, approximately 530 nucleotides of the viral leader sequence and 5' portion of the viral 'gag' gene. Included in the bovine growth hormone segment of the recombinant plasmid are the 5' bovine growth hormone exons (shown in boxes) as well as μ500 5 base pairs found at the 3' terminus of the gene.

100 ng of DNA containing equimolar quantities of the above isolated DNA fragments were ligated for 1 hour at 22° C. Following transfection into E. coli RR1 cells, 100 colonies were isolated. Non-ligated control DNA preparations resulted in zero colonies.

Restriction enzymatic digestion analysis of this cloned DNA confirmed that the two segments of the above mentioned DNAs were joined, thus creating a new biological molecule. This molecule has been termed pBGH-3.

Construction of Recombinant Plasmid, pBGH-4

In order to alter pBGH-3 such that non-essential regions of the Rous Sarcoma derived DNA were removed, the following procedure was followed.

A large 7.0 kb linear DNA fragment derived from pBGH-3 by BSTEII and BamHI cleavage was purified by agarose gel electrophoresis. Following excision from the gel, the DNA was treated with E. coli DNA polymerase (Klenow large fragment) which resulted in the generation of molecules possessing flush termini. Ligation of these molecules and transfection into *E. coli* RR1 cells resulted in bacterial clones containing plasmid DNA similar to that of pBGH-3. However approximately 430 base pairs between the viral BSTEII and BamHI sites have been deleted. Restriction enzymatic digestion analysis of this cloned DNA confirmed that this non-essential region of the pBGH-3 had been removed. This plasmid has been designate pBGH-4.

Sequencing of pBGH-4

The DNA nucleotide sequencing of pBGH-4 was done in the following manner: pBGH-4- DNA (20 ng) was cleaved with EcoRI resulting in 3 linear DNA fragments of 4.3 kb, 2.15 kb, and 1.5 kb. The 2.15 kb DNA molecule was isolated by agarose gel electrophoresis (1% Seaplaque agarose). Following elution of the DNA from the agarose gel, the 5' protruding termini were labeled by addition of $\alpha$-5'($^{32}$P) dATP using *E. coli* DNA polymerase I (Klenow fragment). The $^{32}$P labeled DNA molecule was cleaved subsequently with SmaI yielding 2 DNA molecules of 2.0 kb and 0.5 kb in size. The DNA molecule containing 2.0 kb was purified by agarose gel electrophoresis (1% Seaplaque agarose) and sequenced according to the procedure of Maxam and Gilbert *Proc. Natl. Acad. Sci.* USA, 74: 560-564 (1977). The junction between the RSV-LTR and the bovine growth hormone gene was confirmed to be the predicted sequence:

```
LTR                              BGH
5'  C A T T T G G T G A C  G A T C C C A G G A  3'
3'  G T A A A C C A C T G  C T A G G G T C C T  5'
```

Transient Assay for Screening Plasmid Constructs

We have also developed a rapid and sensitive transient assay system for the detection of bovine growth hormone by cultured rat GH3 cells transfected with plasmid DNA encoding bovine growth hormone, to quickly screen a variety of plasmid constructs for their ability to direct the synthesis of BGH. We have shown and confirmed that pBGH-4 directs the synthesis and secretion of bovine growth hormone by these cells.

The optimum conditions for the transient expression of bovine growth hormone by rat GH3 cells (ATCC 82.1) have been determined.

It has been reported in the literature that DNA transfection of cultured cells mediated by DEAE-Dextran is influenced by at least two parameters. They are (1) the concentration of DNA used in the experiment and (2) the length of time cells are exposed to the DEAE-Dextran-DNA complex. We have optimized our transient assay system in rat GH3 relative to these two parameters.

Briefly about $5.0 \times 10^5$ rat GH3 cells were plated onto 35 mm tissue culture plates. Following overnight incubation, cells were rinsed with 2.0 ml culture fluid minus serum. 1.0 Ml of culture fluid minus serum containing a variety of concentrations of pBGH-4 DNA along with DEAE-Dextran (200 $\mu$g/ml) was added to the cells. Following incubation at 37° C. for a variety of time intervals, the DEAE-Dextran-DNA solution was removed and the cells rinsed two times with complete medium. Cells were incubated for 5 days with changes in cultured fluid at daily intervals. Bovine growth hormone was assayed in the culture fluid using a sensitive radioimmunoassay.

Using this assay, pBGH-4 directed detectable levels of bovine growth hormone, detectable at 48 hours and 72 hours post transfection. Increasing amount of DNA in the DEAE-DNA complex used per transfection resulted in a respective elevation in BGH secretion At 72 hours, cells exposed to 500 ng of DNA produced approximately 10 fold more (283.8 ng/ml) BGH relative to these exposed to 250 ng DNA, (30 ng/ml).

In a similar manner the amount of time to which the cells were exposed to the DEAE-Dextran-DNA mixture was altered. In this experiment, 250 ng of DNA was used in each transfection. Bovine growth hormone expression varied inversely with the duration of transfection time.

From these and other related experiments, and although results do vary from one set of experiments to another, it is concluded that pBGH-4 DNA directs the synthesis of detectable levels of bovine growth hormone by cultured rat GH3 cells following DEAE-Dextran mediated transfection.

The optimum amount of DNA used in these transfection experiments ranged from 250 ng to 500 ng per $5 \times 10^5$ cells.

Time intervals of DEAE-Dextran-DNA exposure to GH3 cells between 30 minutes and 45 minutes are optimal for subsequent expression of bovine growth hormone.

Production of Mouse Cell Lines Secreting Bovine Growth Hormone

In order to produce a large amount of purified BGH protein, we generated cultured mouse fibroblasts secreting the BGH. This was performed by co-transforming mouse TK(−) L cells with Herpes Viral TK DNA and plasmid vectors capable of directing BGH expression as determined by our transient assay. After selecting for a TK(+) phenotype, plasmids encoding BGH will be present and active in directing the expression of Bovine Growth Hormone.

To $5 \times 10^5$ mouse L cells (LTK−, APRT−) was added a complex of calcium phosphate precipitated DNA. Included in the complex was 10 $\mu$g of L cell (LTK−, APRT−) DNA, 10 $\mu$g of pBGH-4 DNA, and 100 ng of pTK5 DNA. Ten TK positive colonies were selected and subcultured. The amount of bovine growth hormone secreted into the culture fluid was determined. Culture L-BGH-4-3 is secreting about 3.0 $\mu$g BGH per $5 \times 10^6$ cells, per 24 hours.

In order to generate a mouse cell line which secrete a larger quantity of BGH, an alternative approach was performed. The protocol involves cotransformation of mouse-L-cells (TK-, APRT-) by a plasmid DNA which encodes the APRT gene and a truncated TK gene, PdLAT-3, (Robert & Axel, 1982) along with plasmid pBGH-4 DNA. Results from these types of cotransformation experiments have revealed that plasmid DNA involved in the cotransformation are amplified within the mouse cell following transfection. Amplification of the plasmid DNA results in a corresponding amplification of gene product (+).

Briefly, $5 \times 10^5$ cells are cotransformed, using the CaPO$_4$ method above, with PdLAT-3 (20 ng) and P-BGH-4 (2 $\mu$g) DNA. The cells are first selected in DME plus 10% CS plus 4 $\mu$g/ml azaserine, plus 15 $\mu$g/ml adenine for selection of the APRT+ phenotype. These APRT+ cells are then selected in DME plus 10%

CS plus 15 μg/ml hypoxanthine plus 1 μg/ml aminopterin plus 5.15 μg/ml thymidine for selection of the TK+ phenotype. The APRT+, TK+ cells are subsequently screened for their ability to secrete BGH. Twenty stable positive colonies were selected and subcultured. The amount of BGH secreted into the culture fluid was determined. Culture L-Pdl)-BGH-4-13 is secreting 75 μg BGH per $5 \times 10^6$ cells per 24 hours.

BGH produced by these cells can be purified as known in the art and used as desired, e.g., as a growth stimulant in animals, see EPO 0085036, Monsanto, and EPO 0068646, Upjohn.

Two mouse L-cell lines stably transformed with pBGH-4 DNA and expressing large amounts of BGH as well as plasmids pBGH-3 and pBGH-4 have been deposited at the ATCC, and are available to be public upon the grant of a patent to the assignee, Merck & Co. Inc., disclosing these. These deposits are also available as required by Foreign Patent laws in countries wherein counterpart applications are filed. The deposit numbers are ATCC CRL-8536 and ATCC CRL-8537, for the mouse cell cultures BGH-4-13 and BGH-4-3, respectively, deposited May 1, 1984; and ATCC 39674 and ATCC 39675, for pBGH-3 and pBGH-4, respectively.

These tissue cultures can be grown in large scale production systems, using techniques known in the art, in order to produce large quantities of the bovine growth hormone. Media, times of incubation, methods of isolating and purification are all familiar to those skilled in the art. For example, purification to obtain crystalline BGH, for use in the cattle industry or for research purposes, can be done by following the procedures, or obvious modifications thereof, given in the article entitled "Purification of Anterior Pituitary Hormones: Bovine, Rat and Rabbit", by L. E. Reichart, Jr., appearing in the book "Methods of Enzymology," vol 37, at p. 360. The book, published in 1975, is available from Academic Press, N.Y.

The use of BGH is disclosed in Machlin, (1973), J. Dairy Science 56: 575–580; C. J. Peel, et al., J. Nutr. (1981), 111(9) 1662–1671; see also EPO application 85036, published Aug. 3, 1983.

Although this invention has been described in terms of bovine growth hormone production, we also contemplate that it encompasses the use of the Rous sarcoma LTR, as fully enabled in U.S. Pat. No. 4,405,712, as a promoter or enhancer in directing gene expression in any eukaryotic cells. Examples of the proteins, in addition to BGH to which the methodology of this application to applicable include human serum albumin, human interferons, human antibodies, human insulin, blood clotting factors, human growth factors, brain peptides, enzymes, prolactin, viral antigens, and plant proteins. The gene to be expressed may be derived from a plant or animal. Particularly useful proteins include human growth hormone gene(s), and poultry growth hormone gene(s).

What is claimed is:
1. Plasmid pBGH-4.
2. A mouse fibroblast cell line containing plasid pBGH-4.
3. The mouse fibroblast cell line BGH-4-3.
4. The mouse fibroblast cell line BGH-4-13.
5. A method of producing bovine growth hormone comprising introducing plasmid pBGH-4 into rat GH3 cells by DEAE-Dextran mediated transfection, and incubating the cells at 37° C. for about 120 hours.

* * * * *